(12) United States Patent
Ozcan et al.

(10) Patent No.: US 9,683,938 B2
(45) Date of Patent: Jun. 20, 2017

(54) FLUORESCENT IMAGING USING A FLATBED SCANNER

(71) Applicant: THE REGENTS OF THE UNIVERSITY OF CALIFORNIA, Oakland, CA (US)

(72) Inventors: Aydogan Ozcan, Los Angeles, CA (US); Zoltan Gorocs, Los Angeles, CA (US); Yuye Ling, New York, NY (US); Meng Dai Yu, Chatsworth, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/906,789

(22) PCT Filed: Jun. 20, 2014

(86) PCT No.: PCT/US2014/043414
§ 371 (c)(1),
(2) Date: Jan. 21, 2016

(87) PCT Pub. No.: WO2015/017046
PCT Pub. Date: Feb. 5, 2015

(65) Prior Publication Data
US 2016/0161409 A1    Jun. 9, 2016

Related U.S. Application Data
(60) Provisional application No. 61/860,525, filed on Jul. 31, 2013.

(51) Int. Cl.
*G02B 26/08*    (2006.01)
*G01N 21/64*    (2006.01)
(Continued)

(52) U.S. Cl.
CPC ..... *G01N 21/6458* (2013.01); *G01N 15/1434* (2013.01); *G01N 15/1456* (2013.01);
(Continued)

(58) Field of Classification Search
CPC ............... G01N 21/64; G01N 21/6458; G01N 15/1434; G01N 15/1456; G01N 21/6456;
(Continued)

(56) References Cited

U.S. PATENT DOCUMENTS 7,015,486 B1    3/2006  Sarbach et al.
9,331,113 B2 *  5/2016  Ozcan .................... G01N 21/64
(Continued)

FOREIGN PATENT DOCUMENTS

WO    WO 2013/086428 A1    6/2013

OTHER PUBLICATIONS

PCT International Search Report for PCT/US2014/043414, Applicant: The Regents of the University of California, Form PCT/ISA/210 and 220, dated Oct. 29, 2014 (5pages).
(Continued)

*Primary Examiner* — Euncha Cherry
(74) *Attorney, Agent, or Firm* — Vista IP Law Group LLP

(57) ABSTRACT

A scanning system for fluorescent imaging includes a sample holder configured to hold a sample therein, the sample holder defining a sample holding region. A scanner head spans the sample holding region and is movable relative to the sample holder. An array of light sources is disposed on an opposing side of the sample holder and is angled relative thereto. Respective controller are operably coupled to the scanner head and the array of light sources, wherein one controller selectively actuates a one or more rows of the array of light sources and another controller controls movement of the scanner head to capture fluorescent light emitted from within the sample holder in response
(Continued)

to illumination from the actuated light sources. A filter designed to filter out scattered light from the sample may be interposed between the sample holder and the scanner head.

20 Claims, 9 Drawing Sheets

(51) Int. Cl.
　　　*G01N 33/50*　　　(2006.01)
　　　*G01N 15/14*　　　(2006.01)
　　　*G01N 33/58*　　　(2006.01)

(52) U.S. Cl.
　　　CPC ......... *G01N 21/6456* (2013.01); *G01N 33/50* (2013.01); *G01N 33/582* (2013.01); *G01N 2201/062* (2013.01); *G01N 2201/068* (2013.01); *G01N 2201/0612* (2013.01); *G01N 2201/101* (2013.01)

(58) Field of Classification Search
　　　CPC .............. G01N 33/50; G01N 33/582; G01N 2201/062; G01N 2201/0612; G01N 2201/068; G01N 2201/101; G01N 15/1463; G02B 21/00; H01L 27/146
　　　USPC ...................................................... 359/204.1
　　　See application file for complete search history.

(56) References Cited

U.S. PATENT DOCUMENTS

| | | |
|---|---|---|
| 2001/0024834 A1 | 9/2001 | Kimura |
| 2003/0058485 A1 | 3/2003 | Otokuni |
| 2011/0006219 A1 | 1/2011 | Schausberger et al. |
| 2012/0099803 A1 | 4/2012 | Ozcan et al. |
| 2012/0148141 A1 | 6/2012 | Ozcan et al. |
| 2012/0157160 A1 | 6/2012 | Ozcan et al. |
| 2012/0218379 A1 | 8/2012 | Ozcan et al. |
| 2012/0248292 A1 | 10/2012 | Ozcan et al. |
| 2012/0281899 A1 | 11/2012 | Ozcan et al. |
| 2013/0092821 A1 | 4/2013 | Ozcan et al. |
| 2013/0157351 A1 | 6/2013 | Ozcan et al. |
| 2013/0193544 A1 | 8/2013 | Ozcan |
| 2013/0203043 A1 | 8/2013 | Ozcan et al. |
| 2013/0258091 A1 | 10/2013 | Ozcan et al. |
| 2013/0280752 A1 | 10/2013 | Ozcan et al. |
| 2014/0120563 A1 | 5/2014 | Ozcan et al. |
| 2014/0160236 A1 | 6/2014 | Ozcan et al. |
| 2014/0300696 A1 | 10/2014 | Ozcan et al. |
| 2015/0111201 A1 | 4/2015 | Ozcan et al. |
| 2015/0153558 A1 | 6/2015 | Ozcan et al. |
| 2015/0204773 A1 | 7/2015 | Ozcan et al. |

OTHER PUBLICATIONS

PCT Written Opinion of the International Search Authority for PCT/US2014/043414, Applicant: The Regents of the University of California, Form PCT/ISA/237, dated Oct. 29, 2014 (5pages).
PCT International Preliminary Report on Patentability (Chapter I of the Patent Cooperation Treaty) for PCT/US2014-043414, Applicant: The Regents of the University of California, Form PCT/IB/326 and 373, dated Feb. 11, 2016 (7pages).
Shaner, Nathan C. et al., A guide to choosing fluorescent proteins, Nat. Methods, vol. 2, No. 12, Dec. 2005, 905-909.
Zhang, Jin et al., Creating New Fluorescent Probes for Cell Biology, Nat. Rev. Mol. Cell Biol., vol. 3, Dec. 2002, 906-918.
Resch-Genger, Ute et al., Quantum dots versus organic dyes as fluorescent labels, Nat. Methods, 5, 763-775 (2008).
Arpali, Serap Altay et al., High-throughput screening of large volumes of whole blood using structured illumination and fluorescent on-chip imaging, Lab Chip, Dec. 7, 2012; 12(23): 4968-4971.
Nagrath, Sunitha et al., Isolation of rare circulating tumour cells in cancer patients by microchip technology, Nature, Dec. 20, 2007; 450(7173):1235-1239.
Stott, Shannon L. et al., Isolation of circulating tumor cells using a microvortex-generating herringbone-chip, Proc. Nat'l. Acad. Sci., U.S.A; Oct. 26, 2010; 107(43); 18392-18397.
Sheng, Weian et al., Aptamer-enabled Efficient Isolation of Cancer Cells from Whole Blood Using a Microfluidic Device, Anal. Chem., May 1, 2012; 84(9); 4199-4206.
Coumans, Frank A. et al., Filter Characteristics Influencing Circulating Tumor Cell Enrichment from Whole Blood, Plos One, 2013, 8, e61770.
Sonnenberg, A., et al, Dielectrophoretic isolation of DNA and nanoparticles from blood, Electrophoresis, 33:2482-2490 (2012).
Loutherback, Kevin et al., Deterministic separation of cancer cells from blood at 10 mL/min, AIP Advances, 2012, 2, 042107-042107-7.
McLeod, Euan et al., Toward giga-pixel nanoscopy on a chip: a computational wide-field look at the nano-scale without the use of lenses, Lab Chip, 2013, 13, 2028-2035.
Mudanyali, Onur et al., Wide-field optical detection of nanoparticles using on-chip microscopy and self-assembled nanolenses, Nature Photon., 7, 247-254 (2013).
Zhu, Hongyin et al., Cost-effective and Rapid Blood Analysis on a Cell-phone, Lab Chip, Apr. 7, 2013; 13(7):1282-1288.
Zhu, Hongyin et al., Optical Imaging Techniques for Point-of-care Diagnostics, Lab Chip, Jan. 7, 2013; 13(1):51-67.
Greenbaum, Alon et al., Imaging without lenses: achievements and remaining challenges of wide-field on-chip microscopy, Nat Methods. Sep. 2012; 9(9):889-895.
Gorocs Zoltan et al., On-Chip Biomedical Imaging, IEEE Rev Biomed Eng., 2013; 6:29-46.
Levin-Reisman, Irit et al., Automated imaging with ScanLag reveals previously undetectable bacterial growth phynotypes, Nature Methods, 7(9):737-739 (Sep. 2010).
Taton, T.A. et al., Scanometric DNA array detection with nanoparticle probes, Science, Sep. 8, 2000; 289 (5485):1757-60.
Yeh Chia-Hsien et al., An immunoassay using antibody-gold nanoparticle conjugate, silver enhancement and flatbed scanner, Microfluid Nanofluid (2009) 6:85-91.
Sullivan Kate et al., High throughput virus plaque quantitation using a flatbed scanner, Journal of Virological Methods, 179, (2012), 81-89.
Stroustrup, Nicholas et al., The Caenorhabditis elegans Lifespan Machine, Nature Methods, 10(7), 665-670 (Jul. 2013).

* cited by examiner

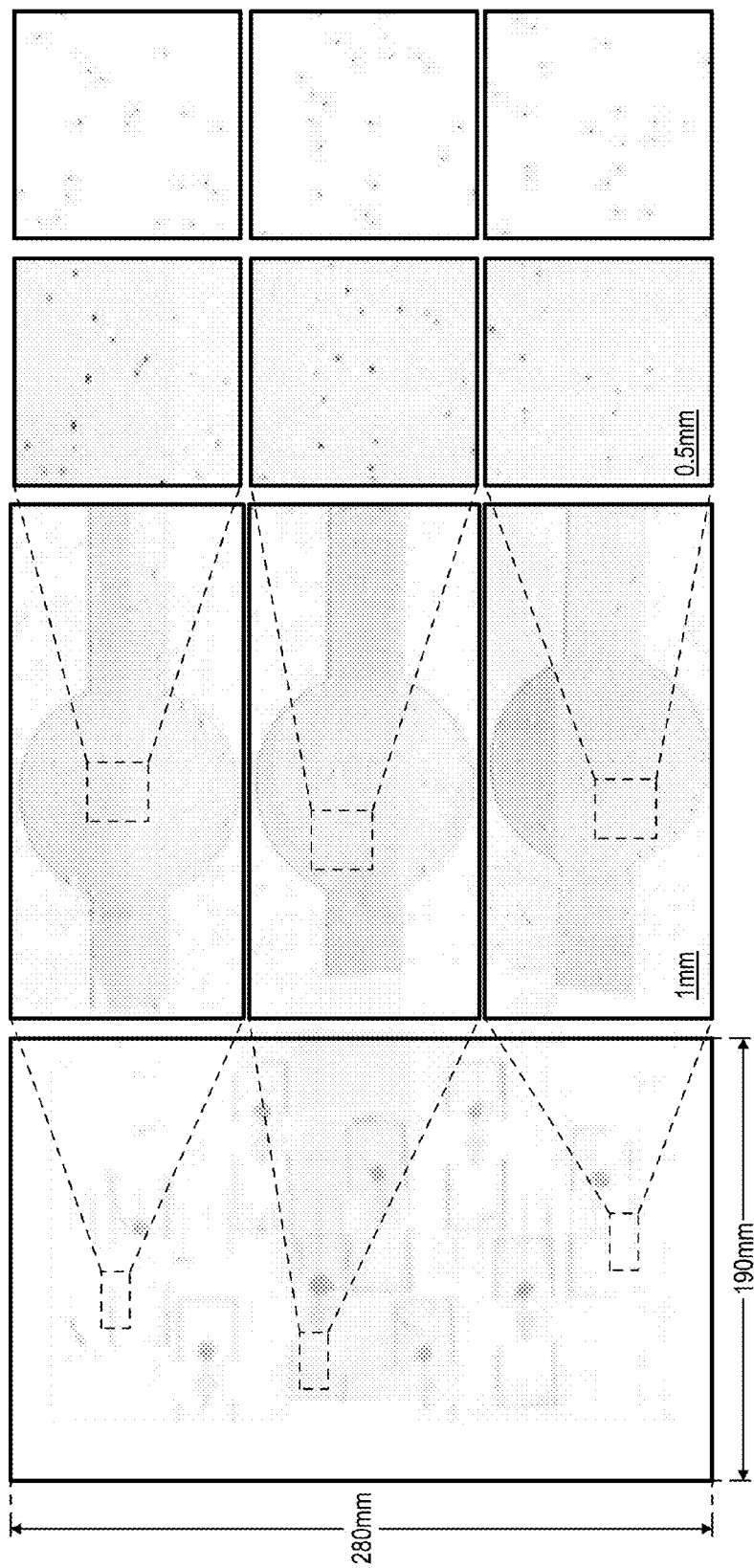

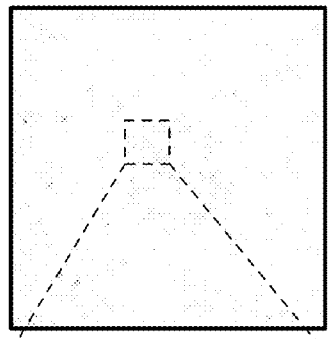 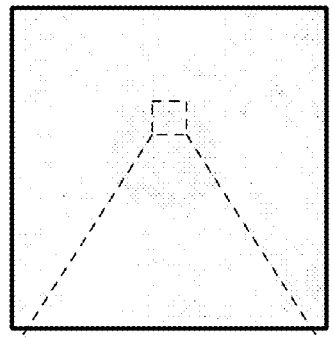 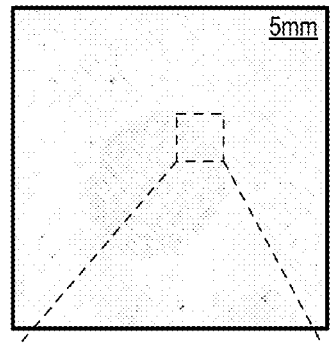
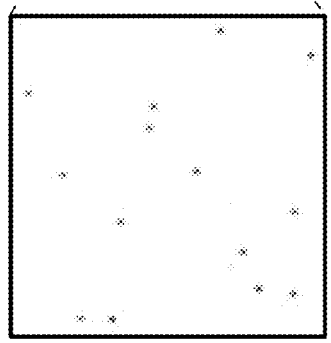 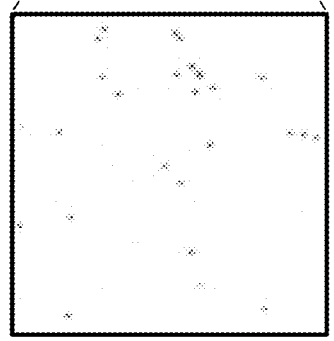 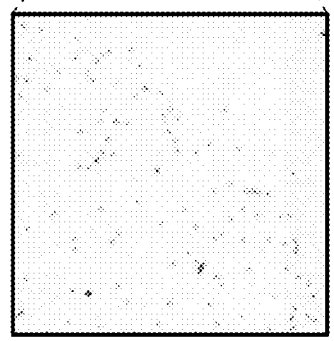
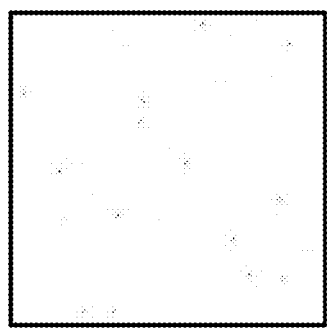 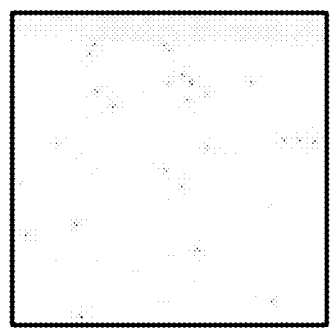 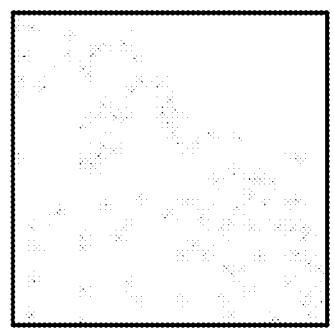
FIG. 10A     FIG. 10B     FIG. 10C

FLUORESCENT IMAGING USING A FLATBED SCANNER

RELATED APPLICATION

This Application is a U.S. National Stage filing under 35 U.S.C. §371 of PCT Patent Application No. PCT/US2014/043414, filed Jun. 20, 2014, which claims priority to U.S. Provisional Patent Application No. 61/860,525 filed on Jul. 31, 2013. The contents of the aforementioned applications are incorporated by reference herein. Priority is expressly claimed in accordance with 35 U.S.C. §§119, 120, 365 and 371 and any other applicable statutes.

FIELD OF THE INVENTION

The technical field generally relates to fluorescent imaging devices and more particularly, scanning devices to screen for fluorescent objects over a large field-of-view (FOV).

BACKGROUND

Several biomedical assays use fluorescent probes or fluorescent labeling due to the specificity and sensitivity that these techniques provide for detection, sensing, and imaging tasks. A major obstacle in using fluorescent labeling for cytometric analysis of cells in bodily fluids is the need for special sample preparation steps, since most of these fluids are optically dense and light scattering, thus it is problematic to excite the fluorescent markers, and challenging to detect their emission due to the strong extinction of the light within the sample. This creates a major challenge in detecting the fluorescent light of labeled cells in, for example, undiluted whole blood which has the characteristic crimson red color. One possible method to circumvent the problem of light extinction is to reduce the height of the microfluidic channel(s) that contain the dense sample. However the shallow depth of field and the relatively small field-of-view (FOV) of conventional optical microscopes result in an observation volume that is typically less than 1 µL. Mechanical scanning stages can increase the observed volume by capturing multiple images, either by moving the microscope objective or the sample itself; however these conventional microscopy based solutions would be rather costly, and would require capturing and digitally processing/stitching over 3,000 partially-overlapping images for screening a volume of e.g., ~1 mL. Digitally processing this many partially-overlapping images is computationally intensive and could easily take many minutes or hours. One alternative method to image fluorescent micro-objects in optically dense media is to use spatially modulated excitation to increase the penetration of the light and use maximum intensity projection algorithms to boost the signal to noise ratio.

Other solutions focus on special sample preparation techniques and smart micro-fluidic chips that are able to extract the target cells with decent specificity and sensitivity from the medium before imaging them. All of these micro-fluidic approaches, however, rely on conventional fluorescent microscopes to image the entire active area of the chip and sometimes capture >5,000 images over a large FOV of 5-10 cm$^2$ to detect the target cells of interest. To mitigate these challenges, there have been various efforts to increase the throughput of fluorescent imaging devices while also aiming to create compact, cost effective, and field-portable solutions for e.g., point-of-care applications. There remains a need for a cost effective fluorescent imaging platform that can rapidly detect fluorescent objects in bodily fluids that tend to extinguish light (e.g., whole blood).

SUMMARY

In one embodiment, a scanning system for fluorescent imaging includes a housing, a sample holder disposed within the housing and configured to hold a sample therein, the sample holder defining a sample holding region having a length (L), width (W) and height (H), wherein L and W>>H. The system includes a scanner head disposed in the housing and movable relative to the sample holder and an array of light sources disposed above the sample holder, the array of light sources substantially covering the sample holding region. An emission filter is interposed between the sample holder and the scanner head. The system includes at least one controller operably coupled to the scanner head and the array of light sources, wherein the at least one controller selectively actuates a subset of light sources of the array and controls movement of the scanner head to capture fluorescent light emitted from within the sample holder in response to illumination from the subset of light sources.

In another embodiment, a scanning system for fluorescent imaging includes a sample holder configured to hold a sample therein, the sample holder defining a sample holding region. The system includes a scanner head spanning the sample holding region and movable relative to the sample holder and an array of light sources disposed above the sample holder and angled relative thereto, the array of light sources substantially covering the sample holding region. An emission filter is interposed between the sample holder and the scanner head. The system includes a first controller operably coupled to the scanner head and a second controller operably coupled to the array of light sources, wherein the second controller selectively actuates a one or more rows of the array of light sources and the first controller controls movement of the scanner head to capture fluorescent light emitted from within the sample holder in response to illumination from the actuated light sources.

In another embodiment, a scanning system for fluorescent imaging includes a sample holder configured to hold a sample therein, the sample holder defining a sample holding region. The system includes a scanner head spanning the sample holding region and movable relative to the sample holder and an array of light sources disposed on the scanner head and substantially covering the sample holding region. An emission filter is optionally interposed between the sample holder and the scanner head. The system includes at least one controller operably coupled to the scanner head and the array of light sources, wherein the at least one controller actuates the light sources and controls movement of the scanner head to capture fluorescent light emitted from within the sample holder in response to illumination from the subset of light sources.

In another embodiment, a method of scanning a sample for fluorescently emitted light includes loading a sample into a scanning system that has a sample holder configured to hold a sample therein; a scanner head movable relative to the sample holder; an array of light sources disposed above the sample holder and angled relative thereto; an emission filter interposed between the sample holder and the scanner head; and at least one controller operably coupled to the scanner head and controlling movement of the scanner head and operably coupled to the array of light sources, wherein the at least one controller selectively actuates one or more rows of light sources of the array. The sample is illuminated with the one or more rows of light sources and an image of the sample is obtained with the scanner head, wherein the image captures fluorescent light emitted from within the sample holder in response to illumination from the one or more rows of light sources.

BRIEF DESCRIPTION OF THE DRAWINGS

FIG. 8A illustrates a fluorescent image of undiluted whole blood spiked with 10 µm fluorescent beads obtained from three separate sample holders of the type illustrated in FIG. 6.

FIG. 8B illustrates magnified regions from the three sample holders of FIG. 8A.

FIG. 8C illustrates additionally magnified regions of FIG. 8B.

FIG. 8D illustrates comparison images taken with a conventional fluorescent microscope of the same regions of the microfluidic chips. Note that due to the liquid state of the sample, minor movement of some fluorescent beads occurred between the two imaging experiments (scanner v. microscope).

FIG. 10A illustrates (top panel) scanned fluorescent images of microscope coverslips containing monolayers of 10 µm fluorescent beads along with zoomed regions of interest (middle panel). The lowermost panel illustrates conventional fluorescent microscope images of the same coverslips for comparison.

FIG. 10B illustrates (top panel) scanned fluorescent images of microscope coverslips containing monolayers of 7 µm fluorescent beads along with zoomed regions of interest (middle panel). The lowermost panel illustrates conventional fluorescent microscope images of the same coverslips for comparison.

FIG. 10C illustrates (top panel) scanned fluorescent images of microscope coverslips containing monolayers of 5 µm fluorescent beads along with zoomed regions of interest (middle panel). The lowermost panel illustrates conventional fluorescent microscope images of the same coverslips for comparison.

DETAILED DESCRIPTION OF THE ILLUSTRATED EMBODIMENTS

Figure 1:
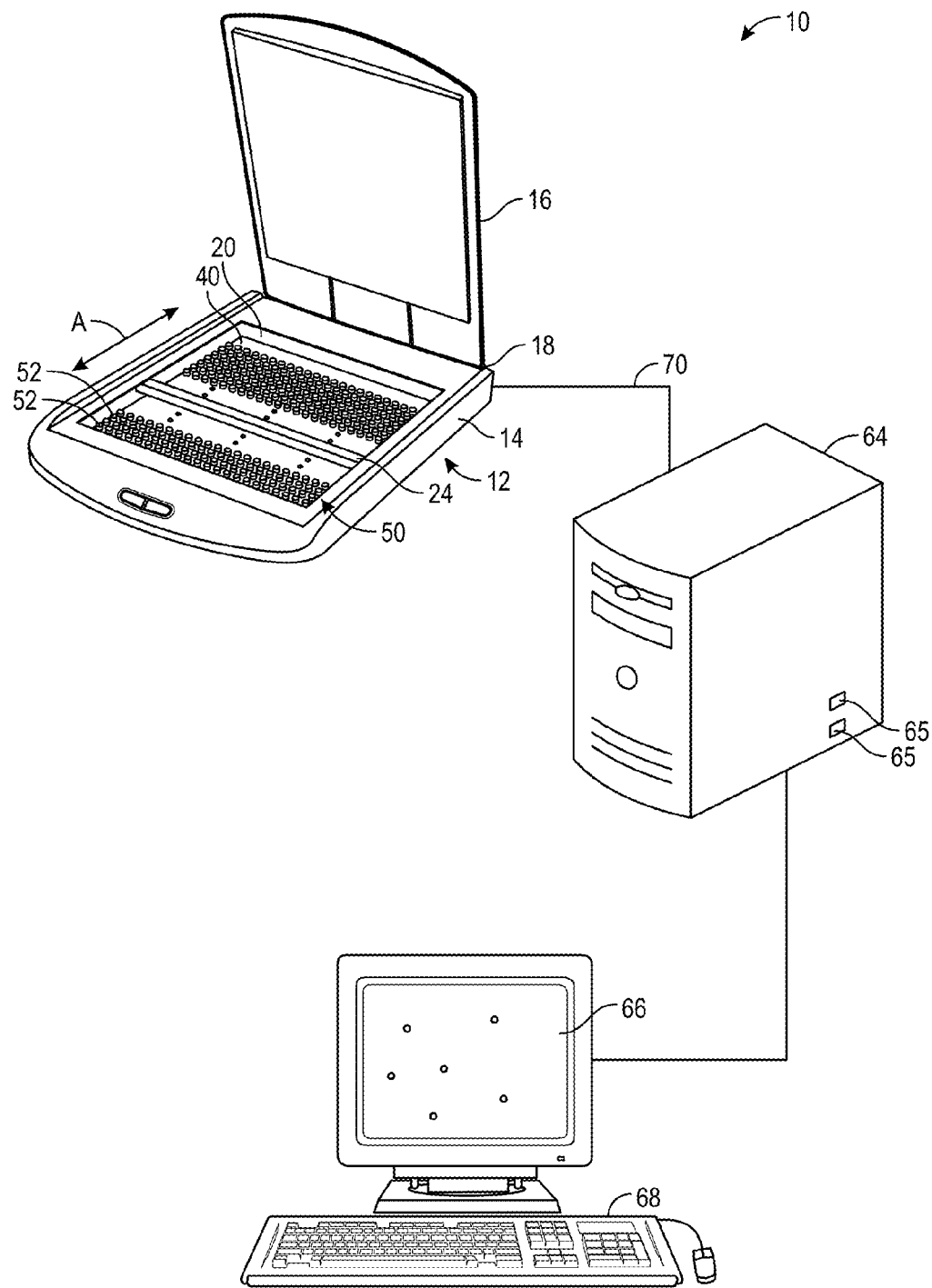
FIG. 1 illustrates a scanning system for fluorescent imaging according to one embodiment.

FIG. 1 illustrates a scanning system 10 for fluorescent imaging according to one embodiment. The scanning system 10 in this embodiment is in the configuration of a flatbed scanner 11. The scanning system 10 includes a housing 12 which encloses various components of the system 10. The housing 12 is typically made from a polymer material such as plastic or the like although other materials may be used. The housing 12 may be formed from multiple components. For example, the housing 12 may have a base 14 and a cover 16 that are connected to one another via a hinge 18 as illustrated. The cover 16 may be used to prevent ambient or environmental light from entering the housing 12. In some embodiments, the cover 16 may be omitted. The housing 12 may optionally have an optically transparent platen 20 such as glass that is used to support a sample holder 40 and other components as explained below. In some embodiments, the optically transparent platen 20 may even form part of the sample holder 40 or it may be omitted entirely in other embodiments. The scanner 11 is connected to a power source such as a standard A/C outlet but could also be powered by a direct current power source.

Figure 3A:
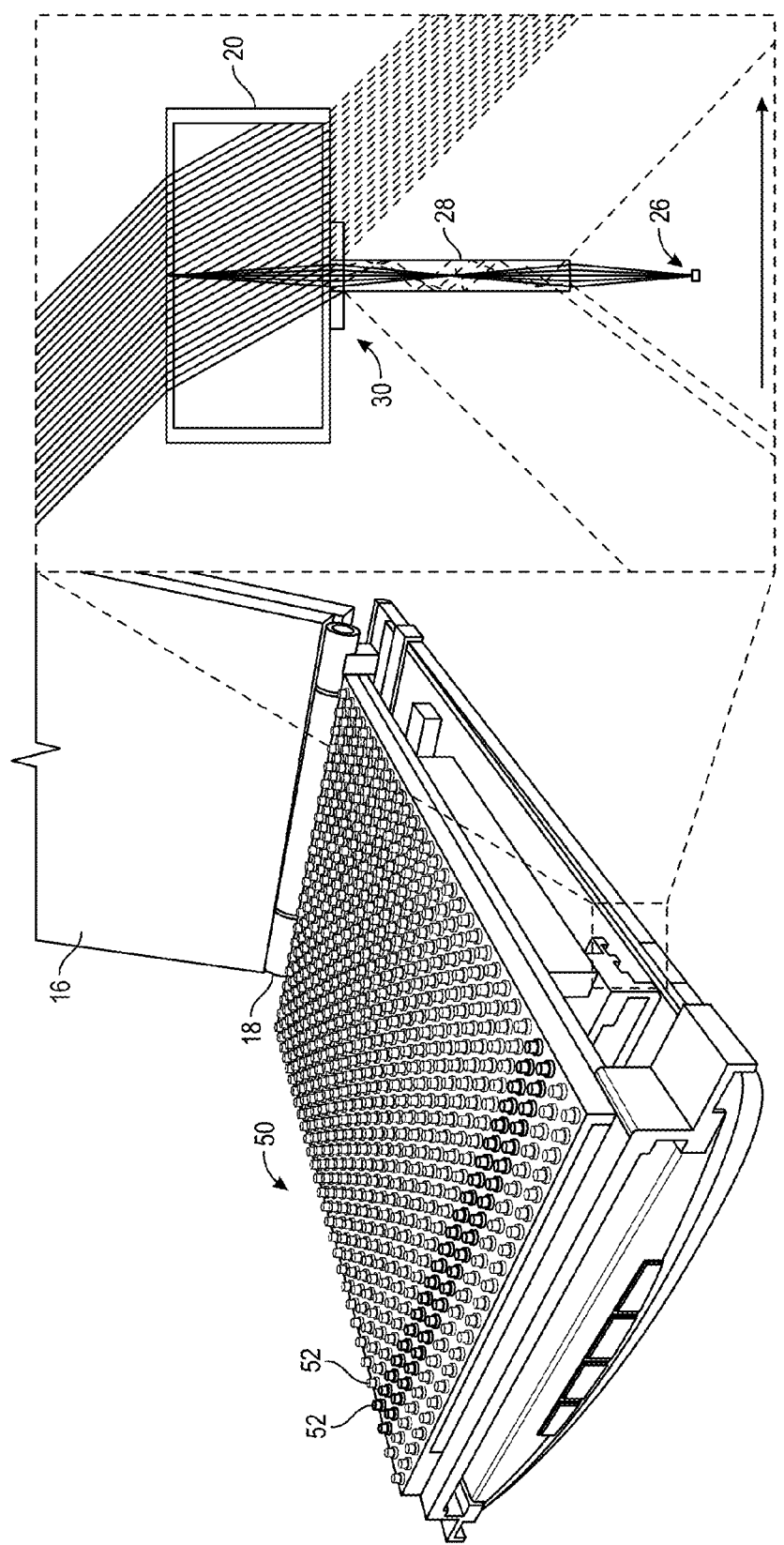
FIG. 3A illustrates a scanner system including a magnified view of the scanner head optics and optically transparent platen.

The scanning system 10 further includes a scanner head 24 that resides within the housing 12 and is moveable in a lateral direction (arrow A in FIG. 1) to scan the sample holder 40. The scanner head 24 is preferably a Contact Image Sensor (CIS) although other types of scanner head 24 configurations can be used (e.g., CCD-based scanners). As best seen in FIG. 3A, the scanner head 24 includes one or more image sensors 26 therein, typically a linear CMOS sensor or multiple linear CMOS sensors aligned in a one dimensional configuration along the length of the scanner head 24. Light is focused onto the image sensor 26 using a self-focusing gradient index lens array 28 located within the scanner head 24. The GRIN lens array 28 is a one dimensional array of GRIN lenses aligned along the length of the scanner head 24. The GRIN lens array 28 has a low numerical aperture (NA) which aids in preventing excitation light from reaching the image sensor 26. In one embodiment, the scanner head 24 includes a filter 30 that permits passage of emitted fluorescent light but blocks scattered excitation light. The filter 30 may be placed on the front side of the GRIN lens array 28. The filter 30 may include a tape or strip that has a substrate on which is deposited an absorptive material such as a dye or the like. In some embodiments, the filter 30 is optional.

Figure 2A:
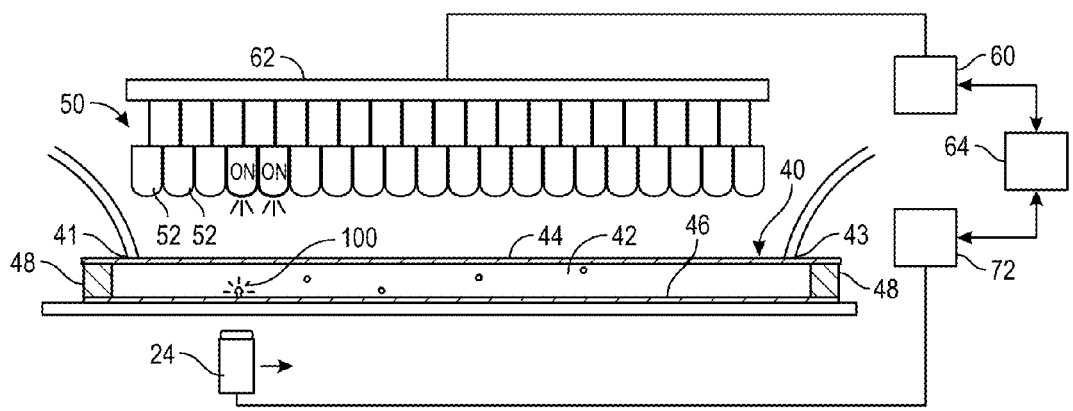
FIG. 2A is a schematic representation of the two-dimensional (2D) light array of light sources, sample holder, and scanner head and control system according to one embodiment.
Figure 2B:
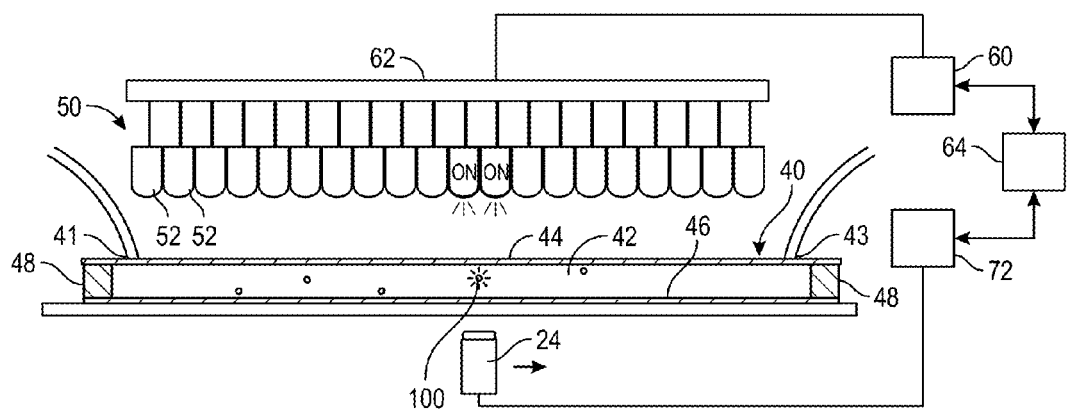
FIG. 2B is a schematic representation of the 2D light array of light sources, sample holder, and scanner head and control system illustrating advancement of the scanner head and actuated rows of light sources.

Returning to FIG. 1, the scanner head 24 is moveable in the direction of arrow A during the scanning process. The scanner head 24 may by driven using a mechanical driver that is commonly used in flatbed scanners. For example, the scanner head 24 may ride along one or more rails that are mounted within the housing 12. The scanner head 24 may be moved back and forth using, for example, a belt coupled to a rotational gear (not shown). As seen in FIG. 1, a sample holder 40 is contained within the housing 12. The sample holder 40 includes a sample holding region 42 or chamber (best seen in FIGS. 2A and 2B) that is dimensioned to receive a sample therein. The sample is typically a liquid but in other alternative embodiments the sample may be a solid or semi-solid (e.g., gel). Referring to FIGS. 2A and 2B, the sample holder 40 may be formed by using a pair of optically transparent substrates 44, 46 that are separated from another using a spacer 48. The spacer 48 defines the height of the sample holding region 42. For example, a sample holder 40 may be formed using a sandwiched structure using polycarbonate substrates 44, 46 that surround a patterned spacer layer 48. For instance, the spacer 48 may be made from patterned, double-sided adhesive tape. The thickness of the spacer may be, for example, tens of microns thick.

Generally, the sample holding region 42 is dimensioned to have a length (L), a width (W), and a height (H) such that L and W>>H. Decreasing the height (H) increases the strength fluorescent signal that is recovered because there is less chance of light extinction. Generally, the height (H) may be in the range of between 60 μm and 100 μm. Instead of using a separate substrate (e.g., substrate 46) for the bottom of the sample holder 40, in some embodiments the bottom layer of the sample holder 40 may utilize the platen 20. In this embodiment, for example, a polycarbonate structure 40 could be adhered to the platen 20 using double-sided adhesive tape forming the spacer 48 that is located directly on the platen 20. In still other embodiments, the sample holder 40 rest on top of the platen 20 as is seen in FIGS. 2A and 2B. Of course, in other embodiments, there is no platen 20 and the sample holder 40 can be directly mounted within the housing 12 to mount the same adjacent to the scanner head 24. In such instances, the sample holder 40 should be mounted within the housing 12 at a distance away from the scanner head 24 to place the focal plane near the bottom of the sample holding region 42.

Figure 2C:
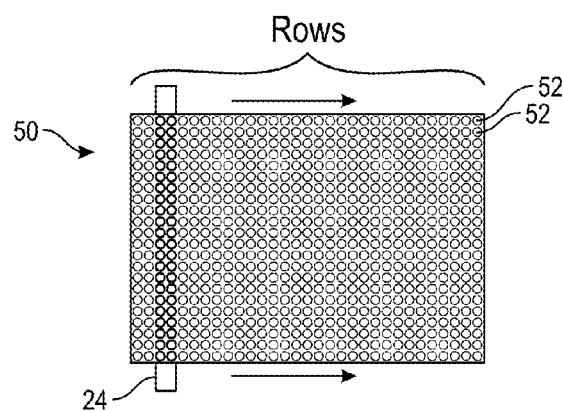
FIG. 2C illustrates a plan view of the 2D light array of light sources and the scanner head. Two rows of the 2D array are actuated (ON).

Still referring to FIG. 1, the system 10 includes an array of light sources 50 that are secured relative to the housing 12 such that the sample holder 40 is interposed between the array of light sources 50 and the scanner head 24. The array of light sources 50 are, in one embodiment, formed from rows and columns of individual light sources 52 such as LEDs or laser diodes. In this embodiment, the array of light sources 50 is configured as a two-dimensional (2D) array. In other embodiments, the array of light sources 50 may include a three-dimensional (3D) array. For example, the array of light sources 50 may include a dome or hemispherical shape although other geometrical arrangements are contemplated. The size of the array of light sources 50 may vary but is large enough to substantially cover the sample holding region 42. FIG. 2C, for example, illustrates twenty (20) rows arranged in thirty (30) columns of individual LEDs 42. As seen in FIGS. 2A and 2B, the array of light sources 50 are coupled to a controller 60 that is selectively drives one or more rows of light sources 52 within the array of light sources 50. The controller 60 (e.g., Arduino microcontroller) may be coupled to optional switching circuitry 62 that is used to selectively actuate or drive row(s) of light sources 52. In this regard, the controller 60 and switching circuitry 62 is able to digitally scan a line of excitation light onto the sample holder 40. The line of excitation light may be light from a single row of light sources 52 or it may be multiple rows as illustrated in FIGS. 2A, 2B, and 2C. FIGS. 2A and 2B illustrate the progression of the "line" of light using selective switching ON/OFF of the individual light sources 50 within a row. Using multiple rows of light sources 52 enables better uniform illumination.

The array of light sources 50 acts, in part, to block out ambient or other environmental light into the interior of the housing 12. However, to ensure that stray light does not enter the interior of the housing 12 and therefore pose a background signal problem, the cover 16 is preferably closed during actuation of the array of light sources 50.

The controller 60 for the array of light sources 50 maybe located external to the housing 12 though in other embodiments it may be integrated into the scanner 11. For example, the controller 60 may be located in or connected to a computing device 64 as seen in FIG. 1. Computing device 64 may include a personal computer, laptop, tablet, Smartphone or the like that includes one or more processors 65 therein that can be used to run software such as the MATLAB program described herein. These can be embodied in any number of electronic devices such as mobile electronic devices such as, but not limited to tablets (e.g., iPads, tablet PCs, mobile phones (e.g., Smartphones)) or even wearable computers such as Google Glass. The computing device 64 is associated with or contains a display 66 that can be used to provide a Graphical User Interface (GUI) to the user. For example, scan results may be displayed on the display 66 that show fluorescent particles 100 contained in the sample. The computing device 64 may be associated with one or more input devices 68 like a keyboard or mouse. The computing device 64 may be connected to the scanner portion 11 of the system 10 using a data communication cable 70 (e.g., USB cable). Of course, data may also be transferred wirelessly between the computing device 64 and the scanner portion 11 of the system 10.

Figure 5:
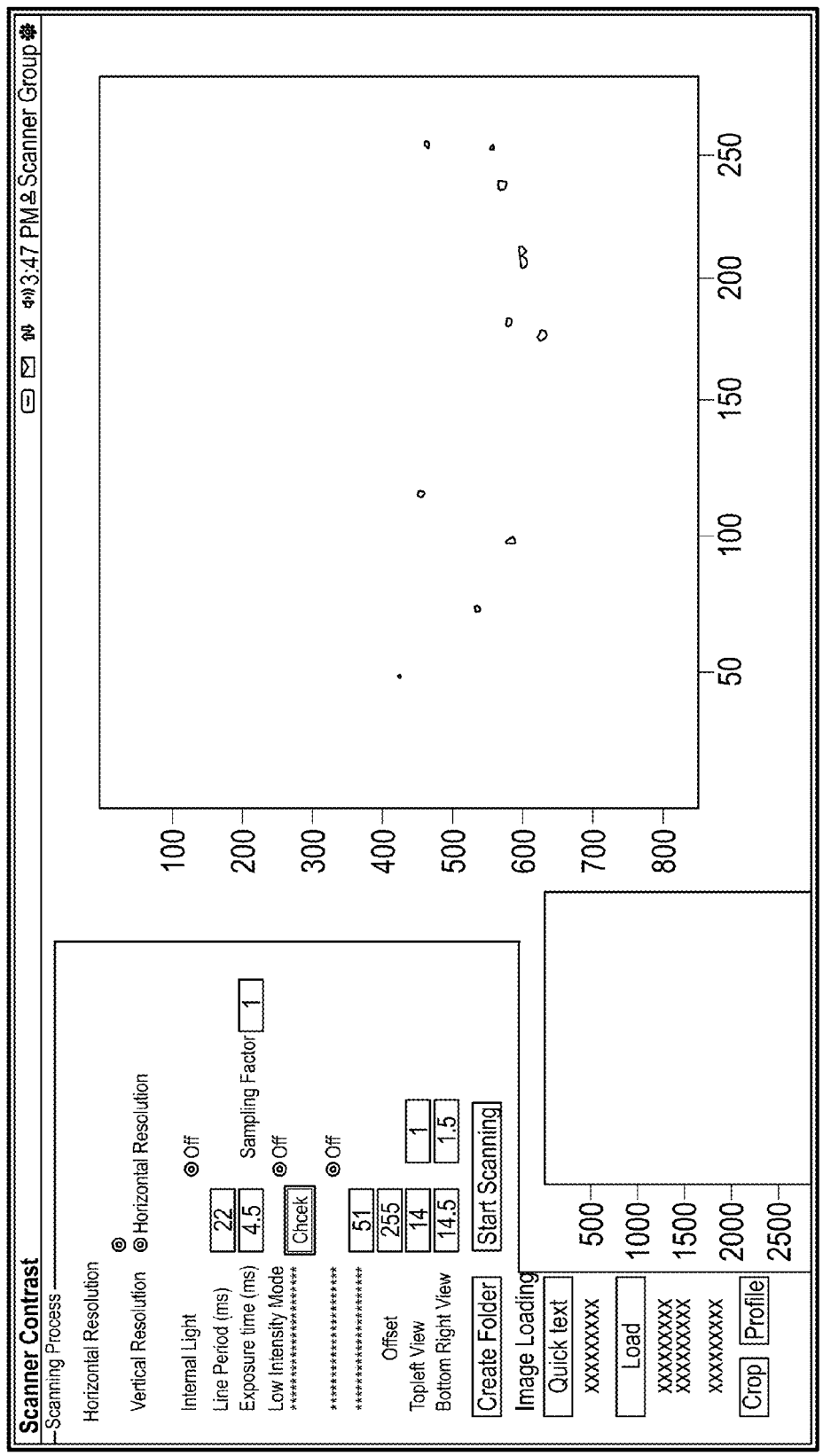
FIG. 5 illustrates a GUI used for the scanning system.

Still referring to FIGS. 2A and 2B, a separate controller 72 is provided for controlling the scanner head 24. The controller 72 may be physically located within the housing 12 of the scanner portion of 11 the device. The controller 72 may be loaded with, for example, driver software that operates the various parameters of the scanner head 24 as well as data acquisition functionality. For example, controller 72 may control parameters of the scanner head 24 such as internal illumination (on/off), area of interest, scanning resolution, AD converter parameters such as offset and gain, Contact Image Sensor (CIS) parameters such as exposure time, gain, shading table, motor movement speed, and motor acceleration/deceleration. The controller 72 may also be used to control data transmission to the computing device 64. In one aspect of the invention, the computing device 64 may be used to install or otherwise load the controller 72 with driver software that is used to operate the scanner head 24 during the fluorescent scanning process. FIG. 5 illustrates an illustrative system GUI that is used for controlling the system 10. Various parameters are presented to the user that can be input and/or adjusted. For example, the internal light the scanner portion may be turned off. The Line Period (ms) and Exposure Time (ms) may be set in addition to the Frontend Gain and Offset. The region to be scanned (top left position and bottom right position) can also be entered. Also displayed in the GUI is in image of the scanned regions with the white dots illustrating areas where fluorescent particles 100 were detected.

In one aspect of the invention, the operation of the controller 60 for the array of light sources 50 is coordinated with the operation of controller 72. For example, it is important that the movement of the scanner head 24 is synchronized with the digital movement of the actuated rows of light sources 52. That is to say, the actuation of the scanner head 24 needs to be coordinated with the triggering of the various rows of light sources 52 so that fluorescent emitted light can be captured by the scanner head 24. In one aspect of the invention, the amount of raw data that is acquired from the scanner head 24 is used as a proxy to determine when one row of light sources 52 should be switched to the next row of light sources 52. The amount of data acquired by the scanner head 24 is proportional to the distance travelled by the scanner head 24 and can be used to establish a cutoff or other threshold that, when exceeded, will cause the controller 60 to instruct switching circuitry to turn on the next adjacent row of light sources 52. Thus, there is no need for any encoder or other sensors that tell the position of the scanner head 24. It should be understood that in some alternative embodiments, a single controller may be used to perform the operations of controllers 60, 72.

Figure 3B:
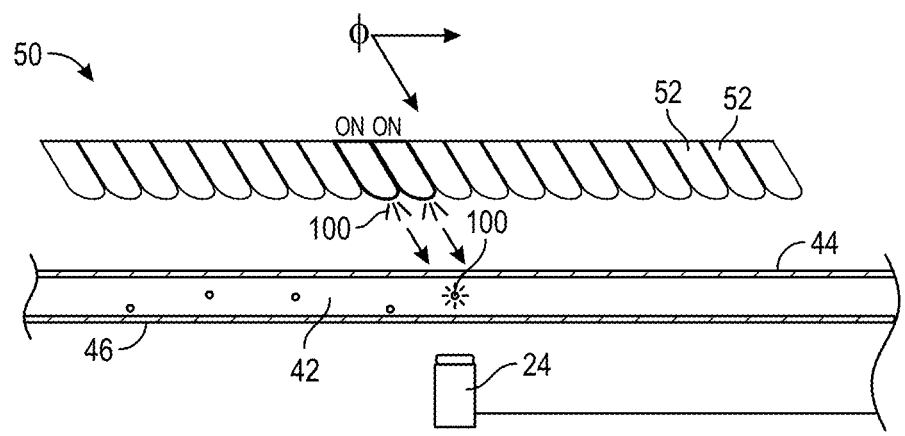
FIG. 3B illustrates an alternative configuration of the 2D light array with the light sources being angled relative to the sample holder.

In one alternative embodiment as illustrated in FIG. 3B, the array of light sources 50 are angled at an angle (θ) relative to the longitudinal axis of the sample holder 40 (e.g., sample plane). Because of the angled orientation of the array of light sources 50, most of the excitation photos are missed by the low numerical aperture (NA) collection optics located at the gradient index lens 28, thereby creating a dark-field background that is required for fluorescent imaging. The angle θ at which the array of light sources 50 are oriented may be within the range of about 5° to about 90°. An angle at or around 45° as explained in the experimental section below provides good results. Note that in this alternative embodiment, as seen in FIG. 3B, the scanner head 24 is not located directly beneath the actuated light sources 52 but is rather laterally offset given the angled orientation of the array of light sources 50.

Figure 4:
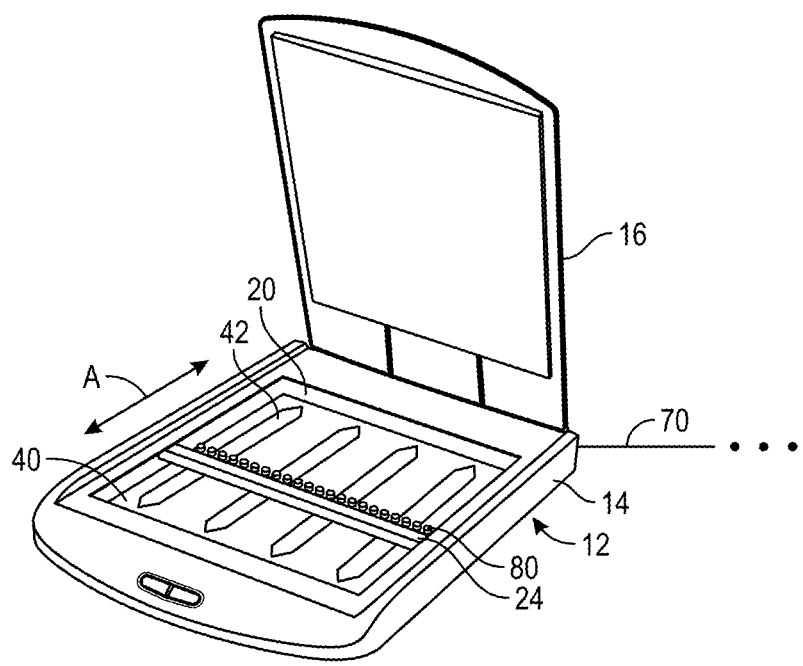
FIG. 4 illustrates a scanning system for fluorescent imaging according to another embodiment.

FIG. 4 illustrates an alternative embodiment of the system 10. In this alternative system 10, similar elements to the embodiment illustrated in FIG. 1 are shown with identical reference numerals. In this embodiment, instead of having an array of light sources, a plurality of light sources 80 is mounted directly on the scanner head 24. The light sources 80 are thus integrated with the scanner head 24. In this alternative embodiment, there is no need for the controller 60 or switching circuitry 62 as the light sources 80 can be turned on when the scanner head 24 is moving, there is no need for digital movement of rows of individual lights sources like in the embodiment of FIG. 1. Another difference illustrated in FIG. 4 is that there is a plurality of sample holding regions 42 contained in the sample holder 40. For instance, each sample holding region 42 may be a separate chamber or lane that is disposed on the optically transparent platen 20. Alternatively, the separate sample holding regions 42 may be integrated into the optically transparent platen 20. The multiple sample holding regions 42 may also be used in connection with the embodiment of FIG. 1. Because the light sources 80 are aimed away from the scanner head 24 in this embodiment, the filter 30 may not be needed. However, the filter 30 may be used to eliminate scattered light.

With reference to FIGS. 2A and 2B, to use the system 10, a sample, such a biological fluid like blood, is loaded into the sample holder 40 via inlet 41 using, for example, conduit or the like. The sample holder 40 has a corresponding outlet 43 that is also connected via a conduit or the like. Of course, a sample can be loaded into the sample holder 40 any number of other ways (e.g., syringe, etc.). In one embodiment of the invention, the sample holding region 42 of the sample holder 40 may be pre-loaded with a capture antibody that is bound to the surface of the sample holding region 42. The capture antibody may be specific to a particular cell, cell type, or cell phenotype, or the like. The biological fluid is loaded into the sample holder 40 whereby if the sample contains the target cell, it will bind to the capture antibody. Reporter antibodies conjugated with fluorescent molecules (e.g., fluorophore) can then be loaded into the device (or concurrently loaded). After the reporter antibodies have formed a sandwich with the captured antigen, the system 10 can then be run to scan the sample holding region 42. The presence of fluorescent light and locations of the same indicate the presence of the target cell. For example, the capture antibody may be designed to capture cancer cells. With reference to FIGS. 2A and 2A, two such fluorescent particles 100 are illustrated. Biological fluid can be loaded into the sample holder 40 and scanned to detect the presence or absence of cancerous cells. This can be performed in a relatively quick manner and does not require pre-processing the sample (e.g., whole blood can be loaded into the system 10). Of course, it should be understood that fluorescent targets do not necessarily have to be bound to an inner surface of the sample holding region 42. In some embodiments, the fluorescent target may be freely contained within the sample fluid. The fluid, however, should be stationary so that particles 100 are stationary as well during the scanning process.

Experimental Data

Methods

In order to create a high-throughput fluorescent imaging platform, a large area microfluidic chip containing the sample was positioned onto a modified flatbed scanner (CanoScan LIDE 200F) as seen in FIG. 3A. The fluorescent excitation was provided by a computer controlled two-dimensional ("2D") array of LEDs, while the scanner's own internal light was turned off. Each LED of the illumination array was tilted by 45° which, in conjunction with the low numerical aperture of the gradient index self-focusing lens array inside the scanner head, ensures that the direct excitation does not reach the sensor array, unless there is a scattering event on the sample plane. To reject such scattered excitation photons, a custom-designed emission filter was created that was then placed directly in front of the self-focusing lens array, significantly reduces the scattered light collection, while also letting the emitted fluorescent light pass through.

This oblique illumination scheme, where the excitation light rays miss the image sensor (see FIGS. 3A and 3B), allows the creation of a very strong dark-field background that is required for fluorescent imaging, without the need for sophisticated and costly fluorescent filters, such as thin-film interference filters. The SANE software driver of the flatbed scanner was also modified to give full control over the scanner features and obtain the highest sensitivity possible by the embedded opto-electronic detector array.

Oblique Illumination Set-Up Using a Digitally Controlled LED Array

To create fluorescent excitation, a 2D array of 30×20 green LEDs (HLMP-CM1A-450DD; 525 nm) was fabricated as illustrated in FIG. 3A. These LEDs are placed 2 cm above the sample plane at an illumination angle of 45° to create the required dark-field background for fluorescent imaging, and to provide uniform illumination over a large FOV, 19 cm×28 cm. Two lines of LEDs (i.e., 20 LEDs×2 rows) are independently controlled and digitally scanned during the forward motion of the scanner head. Therefore, according to the actual position of the scanner head during the image acquisition process, only two lines (e.g., rows) of LEDs are turned on at a given time to considerably reduce the power consumption of the system, and also to reduce the photo bleaching of the sample by only illuminating the immediate surroundings of the area seen by the moving scanner head. In other embodiments, there may only need to be one row of LEDs that is scanned. Laser diodes may be used as an alternative to LEDs. The LEDs were controlled by a computer through an Arduino microcontroller which sequentially turned on two LED rows at a time to follow the sensor during the scan.

Emission Filter Design

In order to create the absorptive material to be used as an emission filter, 0.52 g red dye (Orasol Red BL, BASF) was dissolved in 2 mL of cyclopentanone (≥99%, C112402, Sigma-Aldrich) and used rod coating (LAB3-5W, R.D. Specialties) to deposit a 11 µm layer to an optically clear ~100 µm thick transparent plastic (Mylar®) sheet (AZ42 9×11, Aztec), which was plasma treated before the coating process using a handheld high frequency generator (BD-10AS, Electro-Technic Products). A strip was cut from the coated Mylar® sheet and adhered it to the scanner head directly in front of the self-focusing lens array.

Large-Area Microfluidic Chip Design.

Figure 6:
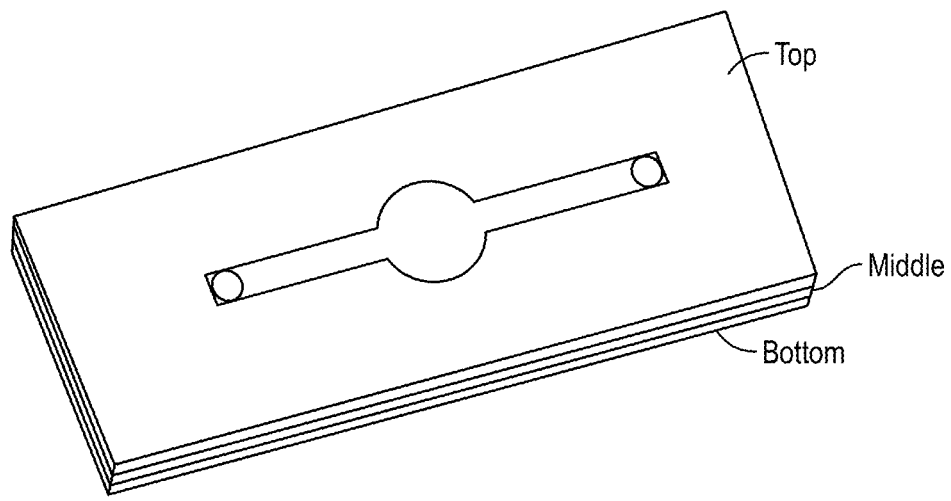
FIG. 6 illustrates one version of a sample holder used to test the fluorescent scanning system.

During measurements two different types of microfluidic chambers were used. First, to validate the performance of the fluorescent scanner a sample holder was created which is compatible with a conventional fluorescent microscope (so that one can easily obtain comparison images). This chamber as seen in FIG. 6 was constructed by aligning and assembling a three layered sandwich structure. For the top layer, a ~1 mm thick polycarbonate rectangle was used with the dimensions of 75 mm×25 mm, which had two 1.7 mm holes for inlet/outlet. The middle layer, which serves as a spacer and creates the required height of the channel, is made of a 60 µm thick double-sided adhesive tape (3M 467 MP). The tape was patterned to create a disc-shaped chamber with 8 mm diameter, and a channel to connect the holes to this volume. The bottom layer, which faces the scanner, is made of a 100 µm thick transparent Mylar® sheet (AZ42 9×11, Aztec). After assembling the sample holder a plastic tube was secured into one of the holes with epoxy to be able to fill it with the liquid sample of interest (See FIGS. 2A and 2B showing similar tubing).

Figure 7:
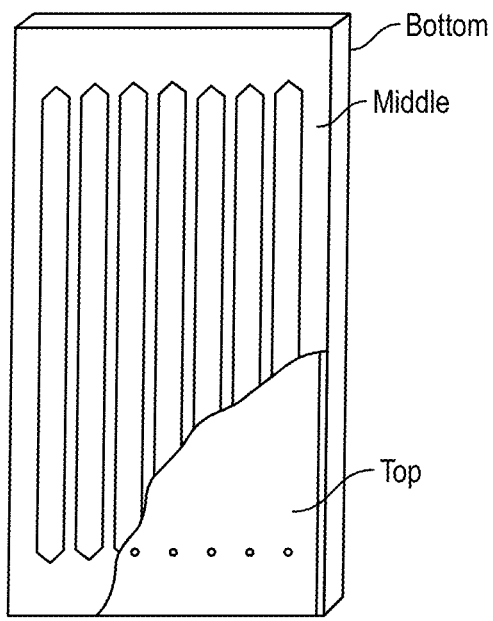
FIG. 7 illustrates another version of a sample holder used to test the fluorescent scanning system.

The second chamber as illustrated in FIG. 7 utilizes the full field of view of the fluorescent scanner and was created by using a similar technique. Here, the sample holder was constructed from a 3 mm thick 19 cm×27 cm polycarbonate sheet as the top layer to increase the stiffness due to the larger chamber size. The spacer is the same 60 µm thick double-sided adhesive tape. The pattern of the tape is such that total area is divided into 7 compartments each with an area of 22 mm×244 mm corresponding to a total volume of 7×322 µL. The scanner's own glass platen was used as the bottom of the chamber due to its high stiffness. Note that the slight variation of the position of the sample with respect to the focal point of the system is negligible due to the large depth of focus and the low NA of the detection optics. The total sample volume held by this chamber design is ~2.2 mL, which is imaged by the fluorescent scanner in <5 minutes.

Sample Preparation

For spiking the fluorescent micro-particles (FluoSpheres 10 µm Red Fluorescent PS Microspheres PSFR010UM, MagSphere) into whole blood samples, 2.5 µL of the particle solution was pipetted into 3 mL of undiluted blood. After careful mixing, the sample is manually injected into the microfluidic chambers using a syringe.

Software Control and Modifications

Control of the scanner was modified to remove all of the image post-processing steps used during conventional document scanning and to increase the fluorescent detection sensitivity. The open source application programming interface (API) package of the Linux operating system called Scanner Access Now Easy (SANE) was used as a starting point. The Canoscan LIDE 200F scanner applies an application specific integrated circuit (Genesys Logic GL847) as its central controller. The control of the scanner is realized by setting the appropriate registers of the controller to the desired values in the data stream sent to the scanner at the beginning of each scan. Since the SANE API has been developed for document scanning additional functionalities were added for fluorescent imaging. Namely, the built-in LED illumination was turned off, since the external LED array is used as described earlier. The calibration step was also turned off as well which sets the gain and the offset of each individual sensor pixel, prior to scanning, based on the scanned image of a white stripe glued to the scanner's document holding glass. In conventional document scanning, this step creates noise free uniform background, but in this implementation it would sacrifice sensitivity and reduce the dynamic range of the fluorescent imager platform. The pixel clock was set to the available minimum frequency to slow down the speed of the scanning and thus increase the exposure time to boost the digital SNR. The gain of the sensor was also increased to its maximum possible value. The output of the device is 14-bit raw intensity information of the fluorescent emission from the sample plane. Note that, unlike 2D color CMOS or CCD sensors, there are no embedded color filters in the flatbed scanner, i.e., it uses a monochrome opto-electronic sensor chip.

Results and Discussion

The performance of the ultra large field of view (19 cm×28 cm) fluorescence imaging system was evaluated by screening spiked fluorescent particles (10 µm diameter) within undiluted whole blood samples injected into nine different microfluidic chips that are distributed across the field of view of the imaging system. In these initial experiments, smaller area micro-fluidic devices were to be able to provide comparison images under a standard fluorescent microscope. Therefore, after the fluorescent scanning experiments, the same samples were also imaged with a regular fluorescent microscope (Olympus BX51) to provide "gold standard" comparison images. Evaluation of the results shown in FIGS. 8A-8C yields a very good match between the scanned fluorescent images and the microscope images in all of the samples, despite the highly scattering and absorbing nature of the blood sample within the microchannel. At the edges of the micro-fluidic chambers the scattering from the sides of the channels partially overlap with the fluorescent signal of the beads, which can be further suppressed with better fluorescent filters and/or different microfluidic chip designs.

Figure 9C:
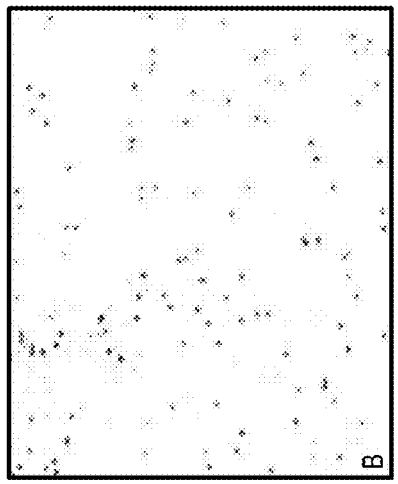
FIG. 9C illustrates zoomed region "B" in FIG. 9A.
Figure 9E:
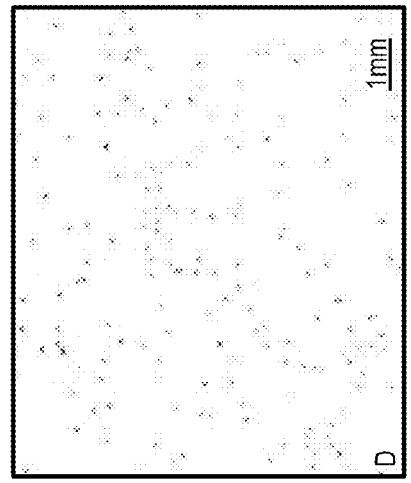
FIG. 9E illustrates zoomed region "D" in FIG. 9A.
Figure 9B:
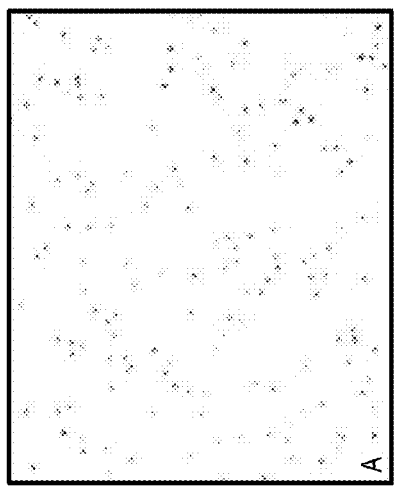
FIG. 9B illustrates zoomed region "A" in FIG. 9A.
Figure 9D:
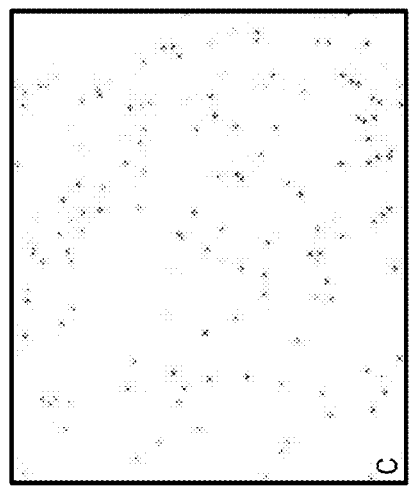
FIG. 9D illustrates zoomed region "C" in FIG. 9A.
Figure 9A:
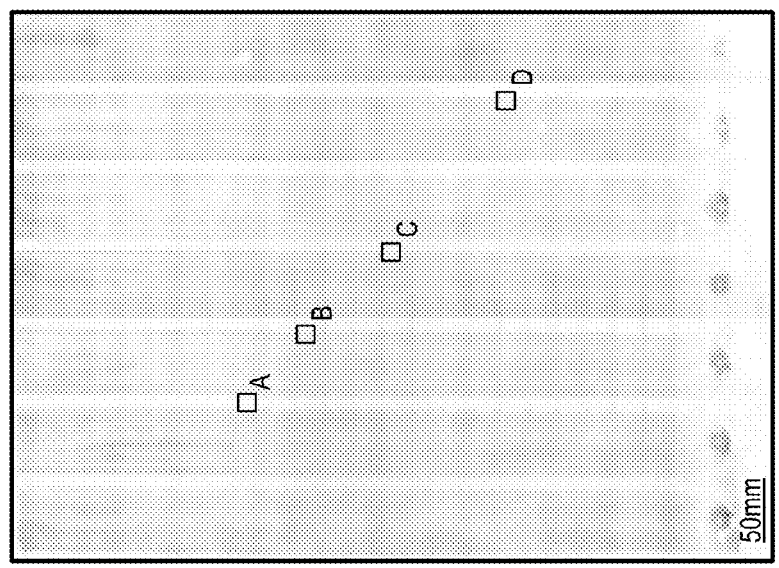
FIG. 9A illustrates full field-of-view fluorescent scan of a sample holder like that of FIG. 7 loaded with whole blood spiked with 10 µm fluorescent beads.

Next, imaging experiments were performed using a large area microfluidic sample holder to demonstrate that a total volume of more than 2.2 mL of whole blood can be screened for fluorescent micro-particles in less than 5 minutes. FIG. 9A illustrates a full field-of-view fluorescent scan of the second chambers of FIG. 7. FIGS. 9B-9E illustrate various zoomed regions obtained from the full FOV scan of FIG. 9A. These scanning results also provide a good match to conventional fluorescent microscope images of the same samples, and further illustrate the rapid and accurate detection of fluorescent micro-objects within large volumes of optically dense and scattering media. These results, combined with the inexpensive materials and technologies used to create this fluorescent imaging platform, lead to a cost effective method for wide-field fluorescent imaging and cytometry. In addition to these, the presented ultra-wide field fluorescent imaging device still maintains the ease of use and portability of a regular flatbed scanner.

The sensitivity of the device was measured by using fluorescent micro-beads of various sizes (5 µm, 7 µm, 10 µm) that were smeared on microscope coverslips. The acquired scanning images of the platform were compared to regular fluorescent microscope images which also provided a good agreement to the results even for 5 µm beads as seen in FIGS. 10A-10C. Since the intensity of the scattered light from non-fluorescent objects within the sample (such as dust particles) is not completely blocked by the custom-designed, cost-effective absorption filter, such unwanted particles can also create a signal that is comparable to the intensity of fluorescent objects that are smaller than 5 µm. To image even smaller particles, this leakage can be avoided by using more advanced filters (e.g., thin film interference filters) to better reject the scattered excitation light before it is collected by the self-focusing lens-array of the platform.

A fluorescent imaging system has been demonstrated that can screen for fluorescent micro-objects over a record-large FOV of ~532 cm$^2$. Of course, it should be understood that smaller FOVs can be used. For instance, the system may be used where FOVs exceed those over 10 cm$^2$. This ultra-large FOV of the imaging platform allows one to screen >2.2 mL of undiluted whole blood for detection of fluorescent micro-objects within <5 minutes, making this high-throughput fluorescent imaging platform especially useful for rare cell research and cytometry applications. Smaller sample volumes may also be used, for example, samples having volumes greater than about 0.1 mL. The system may also be used for other biological samples such as urine or other bodily fluids.

Various modifications can be made to the embodiments illustrated herein. For example, in some embodiments, the sample holder 40 may be integrated with or formed in the platen 20 of the scanner. In still other embodiments, the platen 20 may be omitted entirely. In addition, while two separate controllers 60, 72 are described for controlling the array of light sources 50 and scanner head 24, respectively, a single controller could be used instead of two separate controllers. While green colored light sources 52 have been described herein, the excitation light may be in any number of colors depending on excitation wavelength of the fluorophores in the sample.

While embodiments of the present invention have been shown and described, various modifications may be made without departing from the scope of the present invention. The invention, therefore, should not be limited, except to the following claims, and their equivalents.

What is claimed is:

1. A scanning system for fluorescent imaging comprising:
    a housing;
    a sample holder disposed within the housing and configured to hold a sample therein, the sample holder defining a sample holding region having a length (L), width (W) and height (H), wherein L and W≥H;
    a scanner head disposed in the housing and movable relative to the sample holder;
    an array of light sources disposed above the sample holder, the array of light sources substantially covering the sample holding region;
    an emission filter interposed between the sample holder and the scanner head; and
    at least one controller operably coupled to the scanner head and the array of light sources, wherein the at least one controller selectively actuates a subset of light sources of the array of light sources and controls movement of the scanner head to capture fluorescent light emitted from within the sample holder in response to illumination from the subset of light sources.

2. The scanning system of claim 1, wherein the array of light sources comprise LEDs or laser diodes.

3. The scanning system of claim 1, wherein the array of light sources are angled relative to the sample holder.

4. The scanning system of claim 3, wherein the array of light sources are angled relative to the sample holder within the range of about 5° to about 90°.

5. The scanning system of claim 1, wherein the subset of light sources comprises a linear array of light sources.

6. The scanning system of claim 1, wherein the subset comprises one or more adjacent rows of light sources.

7. The scanning system of claim 1, wherein the at least one controller is operably connected to a computing device.

8. The scanning system of claim 1, wherein the emission filter is disposed on the scanner head.

9. The scanning system of claim 1, wherein the sample holder holds a volume of greater than 0.1 mL.

10. The scanning system of claim 1, wherein the scanning system has a FOV of over 10 cm$^2$.

11. The scanning system of claim 1, further comprising a fluorescent dye kit having a dye configured to be added to the sample holder.

12. The scanning system of claim 1, wherein the system further comprises an optically transparent platen and the sample holder is disposed on the platen.

13. The scanning system of claim 1, wherein the system further comprises an optically transparent platen and the sample holder is integrated into the platen.

14. A method of using the system of claim 1 comprising:
    loading a sample into the sample holder containing fluorescent species;
    illuminating the sample with the array of light sources; and
    obtaining an image of the sample with the scanner head.

15. The method of claim 14, wherein the sample comprises a biological sample.

16. The method of claim 15, wherein the sample comprises blood, urine, or other bodily fluids.

17. A scanning system for fluorescent imaging comprising:
    a sample holder configured to hold a sample therein, the sample holder defining a sample holding region;
    a scanner head spanning the sample holding region and movable relative to the sample holder;
    an array of light sources disposed on the scanner head and substantially covering the sample holding region;
    an emission filter interposed between the sample holder and the scanner head; and
    at least one controller operably coupled to the scanner head and the array of light sources, wherein the at least one controller actuates a subset of light sources of the array of light sources and controls movement of the scanner head to capture fluorescent light emitted from within the sample holder in response to illumination from the subset of light sources.

18. A method of scanning a sample for fluorescently emitted light comprising:
    loading a sample into a scanning system comprising:
        a sample holder configured to hold a sample therein;
        a scanner head movable relative to the sample holder;
        an array of light sources disposed above the sample holder and angled relative thereto;
        an emission filter interposed between the sample holder and the scanner head; and
        at least one controller operably coupled to the scanner head and controlling movement of the scanner head and operably coupled to the array of light sources, wherein the at least one controller selectively actuates one or more rows of light sources of the array;
    illuminating the sample with the one or more rows of light sources; and obtaining an image of the sample with the scanner head, wherein the image captures fluorescent light emitted from within the sample holder in response to illumination from the one or more rows of light sources.

19. The method of claim 18, wherein the sample comprises a bodily fluid.

20. The method of claim 17, wherein a first controller is operably coupled to the scanner head and wherein a second controller is operably coupled to the array of light sources, wherein the second controller selectively actuates a one or more rows of the array of light sources and the first controller controls movement of the scanner head to capture fluorescent light emitted from within the sample holder in response to illumination from the actuated one or more rows of the array of light sources.

* * * * *